United States Patent [19]

Fayter, Jr.

[11] 4,380,656

[45] Apr. 19, 1983

[54] 2-VINYL- AND 2-ETHYLCYCLOPROPANE CARBOXYLATES

[75] Inventor: Richard G. Fayter, Jr., Fairfield, Ohio

[73] Assignee: Emery Industries, Inc., Cincinnati, Ohio

[21] Appl. No.: 287,395

[22] Filed: Jul. 27, 1981

[51] Int. Cl.³ .................. C07D 69/743; C07D 69/747
[52] U.S. Cl. .............................. 549/473; 260/465 D;
548/131; 548/132; 548/187; 548/204; 548/213;
548/214; 548/518; 548/519; 548/523; 548/542;
548/547; 548/551; 548/562; 549/66; 549/79;
549/479; 549/500; 560/124
[58] Field of Search ...................... 260/326.44, 326.46,
260/347.4, 465 D; 548/131,132, 187, 204, 213,
214, 518, 519, 523, 542, 547, 551, 562; 549/66,
79, 473, 479, 500; 560/124

[56] References Cited

U.S. PATENT DOCUMENTS 4,178,463 12/1979 Gittos et al. .......................... 562/574
4,321,406 3/1982 Fayter .................................. 560/124

OTHER PUBLICATIONS

Abraham, Chemical Abstracts, vol. 81 (1974) 77518p.
Danishefsky et al., Chemical Abstracts, vol. 82 (1975) 86259u.
Gittos et al., Chemical Abstracts, vol. 91 (1979) 91499n.
Cho et al., Chemical Abstracts, vol. 92 (1980) 22860g.

Primary Examiner—Richard Raymond
Attorney, Agent, or Firm—Kenneth D. Tremain; Gerald A. Baracka

[57] ABSTRACT

Novel 2-vinyl- and 2-ethylcyclopropane carboxylates useful as pesticides, herbicides and chemical intermediates are provided. The products of this invention contain two gem carboxylate

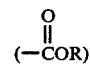

groups, which can be the same or different. The carboxylate groups will contain an aliphatic, cycloaliphatic, aromatic, heteroalkyl or heterocyclic moiety.

7 Claims, No Drawings

2-VINYL- AND 2-ETHYLCYCLOPROPANE CARBOXYLATES

BACKGROUND OF THE INVENTION

1. Field of the Invention

The present invention is directed to novel cyclopropane compounds, and more specifically to 2-vinyl- and 2-ethylcyclopropane-1,1-dicarboxylates, which are useful as pesticides, herbicides and as chemical intermediates.

2. Discussion of the Prior Art

Pyrethrin and various synthetic compounds modeled thereafter, such as allethrin, are widely recognized for their insecticidal activity. In view of great demand for these products and the need to modify certain properties of these products to make them adaptable for other uses, much effort has been directed to the synthesis of structurally related compounds, i.e., compounds based on the 2-vinylcyclopropane structure.

Lower alkyl 2-vinylcyclopropane-1,1-dicarboxylates are reported. For example, Kierstead et al. (J. Chem. Soc., 1952, 3610-21 and J. Chem. Soc., 1953, 1799) report the preparation of diethyl 2-vinylcyclopropane-1,1-dicarboxylate by the condensation of 1,4-dibromo-2-butene and ethyl sodiomalonate. Heretofore known 2-vinylcyclopropane-1,1-dicarboxylates have, however, been limited to the simple ester products, i.e., lower alkyl esters, due to the limitations of the malonic ester condensation procedure by which the products are obtained and the instability of the compounds due to the presence of gem carboxyl groups. The tendency of gem carboxyl groups to dicarboxylate at elevated temperatures is well known.

SUMMARY OF THE INVENTION

Novel esters of cyclopropane useful as pesticides, herbicides and chemical intermediates and having two carboxylate groups in the 1-position of the ring, i.e. gem carboxylate groups, and a vinyl or ethyl moiety in the 2-position have been prepared. The compounds of this invention are highly useful in view of their structural similarity to chrysanthemic acid derivatives and are readily and economically produced utilizing conventional chemical processes.

The cyclopropane compounds of this invention correspond to the general formula

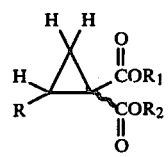

where R represents an ethyl or vinyl group, $R_1$ represents hydrogen, an aliphatic, cycloaliphatic or aromatic hydrocarbon radical having 1 to 30 carbon atoms or an aliphatic, cycloaliphatic or aromatic moiety containing one or more oxygen, sulfur, nitrogen or halogen atoms, and $R_2$ represents a hydrocarbon radical having 1 to 30 carbon atoms or an aliphatic, cycloaliphatic or aromatic moiety containing one or more oxygen, sulfur, nitrogen or halogen atoms, with the proviso that when $R_1$ is hydrogen or an aliphatic hydrocarbon radical having from 1 to 4 carbon atoms, i.e., a $C_{1-4}$ alkyl group, $R_2$ cannot be an alkyl group having fewer than 5 carbon atoms.

Especially useful compounds of this invention are those wherein $R_1$ is an alkyl group having from 1 to 4 carbon atoms and $R_2$ is a radical having 3 to 20 carbon atoms and selected from the group

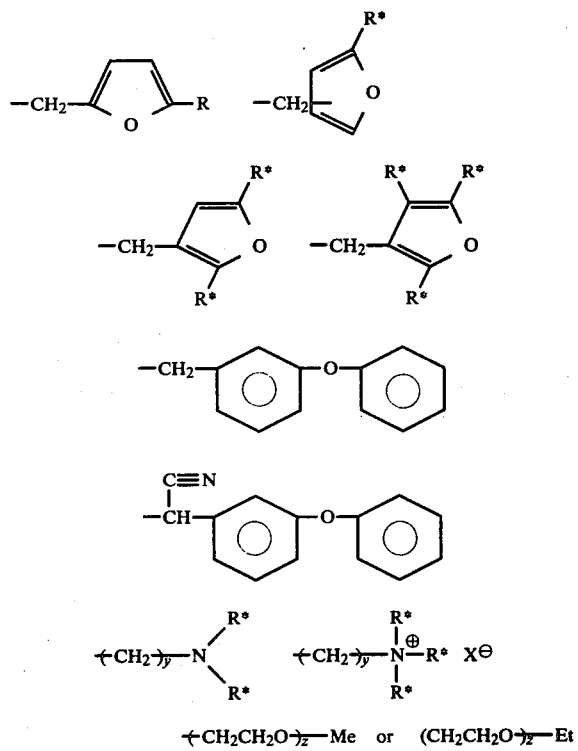

where R* is a $C_{1-4}$ alkyl, $C_{1-4}$ alkenyl, $C_{1-4}$ hydroxyalkyl, phenyl or benzyl, Me is methyl, Et is ethyl, y is an integer from 2 to 6, z is an integer from 1 to 10 and X represents an anion such as a halide, hydroxide, sulfate, nitrate, acetate, alkylsulfate, alkylphosphate, fluoroborate and the like.

DETAILED DESCRIPTION

The novel cyclopropane compounds of this invention correspond to the general formula

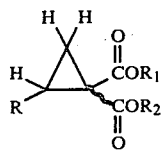

where R represents an ethyl or vinyl group, $R_1$ represents hydrogen, a hydrocarbon radical or an aliphatic, cycloaliphatic or aromatic moiety containing one or more oxygen, sulfur, nitrogen or halogen atoms, and $R_2$ represents a hydrocarbon radical or an aliphatic, cycloaliphatic or aromatic moiety containing one or more oxygen, sulfur, nitrogen or halogen atoms, with the proviso that when $R_1$ is hydrogen or an aliphatic hydrocarbon radical having from 1 to 4 carbon atoms, i.e. a $C_{1-4}$ alkyl group, $R_2$ cannot be an alkyl group having fewer than 5 carbon atoms. Hydrocarbon radicals from which $R_1$ and $R_2$ are selected typically contain from 1 to 30 carbon atoms and can be aliphatic, cycloaliphatic or aromatic or may contain a combination of such moieties.

Useful aliphatic hydrocarbon radicals will contain from 1 to 30 carbon atoms and they may be straight-chain or branched, saturated or unsaturated. Especially useful aliphatic radicals have from 1 to 20 carbon atoms with no more than one double bond for every four carbon atoms.

Cycloaliphatic hydrocarbon radicals may be saturated or unsaturated and may contain one or more hydrocarbon substituents on the ring. These radicals can contain from 3 to 30 carbon atoms, however, preferred cycloaliphatic radicals contain from 5 to 20 carbon atoms and correspond to the formula

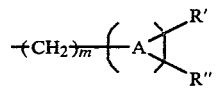

where m is an integer from 0 to 8, and more preferably 0 to 4, A represents a non-aromatic 5- or 6-membered carbon ring system, and R' and R" are hydrogen, a $C_{1-8}$ alkyl or alkenyl group, phenyl or benzyl. Particularly advantageous cycloaliphatic radicals of the above type are those wherein the moiety

is an unsubstituted or mono- $C_{1-8}$ alkyl- or alkenyl-substituted cyclopentyl, cyclopentenyl, cyclohexyl, cyclohexenyl or cyclohexa-2,4-dienyl group.

Aromatic hydrocarbon radicals of the above types will contain from 6 up to about 30 carbon atoms and may consist of a single ring or fused-ring system which can be unsubstituted or have one or more hydrocarbon groups substituted thereon. The aromatic radicals preferably contain from 6 to 20 carbon atoms and correspond to the formula

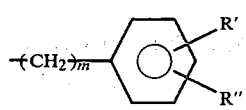

where m is an integer from 0 to 8, and more preferably 0 to 4, and R' and R" are hydrogen, a $C_{1-8}$ alkyl or alkenyl group, phenyl or benzyl. Particularly useful aromatic radicals include phenyl, $C_{1-8}$ alkyl- or alkenyl-substituted phenyl, benzyl and $C_{1-8}$ alkyl- or alkenyl-substituted benzyl.

In addition to the aforementioned hydrocarbon radicals, $R_1$ and $R_2$ can also be independently selected from aliphatic, cycloaliphatic or aromatic moieties which contain one or more oxygen, sulfur, nitrogen or halogen atoms, or a combination thereof. These radicals can result from the substitution of a functional group on an aliphatic, cycloaliphatic or aromatic hydrocarbon radical, such as those previously described, or in the case of oxygen, sulfur and nitrogen, the atoms may be an integral part of a hydrocarbon chain or ring structure, i.e., $R_1$ and $R_2$ are heteroalkyl or heterocyclic radicals.

In the situation when the aliphatic, cycloaliphatic, or aromatic group is substituted with a functional group, the substituent may be halogen, (fluorine, chlorine, bromine or iodine), nitro, amine, nitrile, thionitrile, isothionitrile, mercapto, hydroxy and the like. One or more of these groups may be substituted on the hydrocarbon chain or ring system which can contain up to 30 carbon atoms. $R_1$ and $R_2$ can also be oxo-alkyl or oxo-cycloalkyl radicals such as, for example,

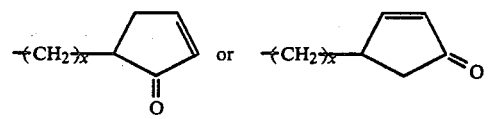

where x is 0 or 1 and the various ring positions may be substituted with a $C_{1-4}$ alkyl or alkenyl, phenyl, benzyl or phenoxy group.

In another embodiment of the invention, the oxygen, sulfur and nitrogen atoms form an integral part of the hydrocarbon chain or hydrocarbon ring system which can contain up to 30 carbon atoms. Illustrative groups of the former type, i.e. heteroalkyl radicals, are radicals derived from alkanolamines, such as ethanolamine; N,N-dialkylalkanolamines, such as N,N-dimethylethanolamine, and quaternized derivatives thereof; monoalkyl esters of polyalkylene glycols, such as diethylene glycol, and higher poly(oxyalkylene) glycols; and the like.

$R_1$ and $R_2$ can also be a heterocyclic group having up to 30 carbon atoms, in which case the oxygen, nitrogen or sulfur atom forms a ring structure, most usually a 5- or 6-membered ring, or fused ring structure thereof. More than one heteroatom may be present in the ring and the heteroatoms need not be the same. Illustrative heterocyclic groups of this type include:

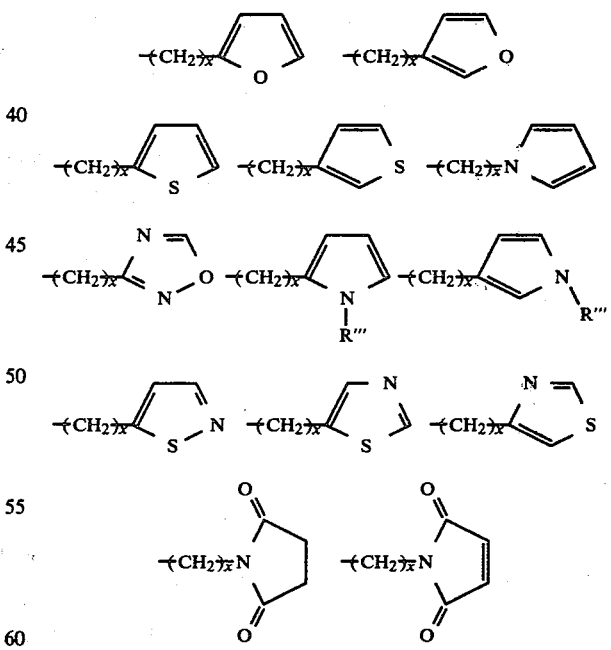

wherein x is 0 or 1, R''' is hydrogen or $C_{1-4}$ alkyl, and each of the available ring positions may be substituted with a $C_{1-4}$ alkyl or alkenyl, phenyl, benzyl or phenoxy group and wherein hydrocarbon groups on adjacent positions may be joined to form a ring.

In an especially preferred embodiment of this invention, $R_1$ is an alkyl group having from 1 to 4 carbon atoms and $R_2$ is a radical containing an oxygen and/or nitrogen atom and having from 3 to 20 carbon atoms. Particularly useful compounds of this type are those wherein $R_2$ is selected from

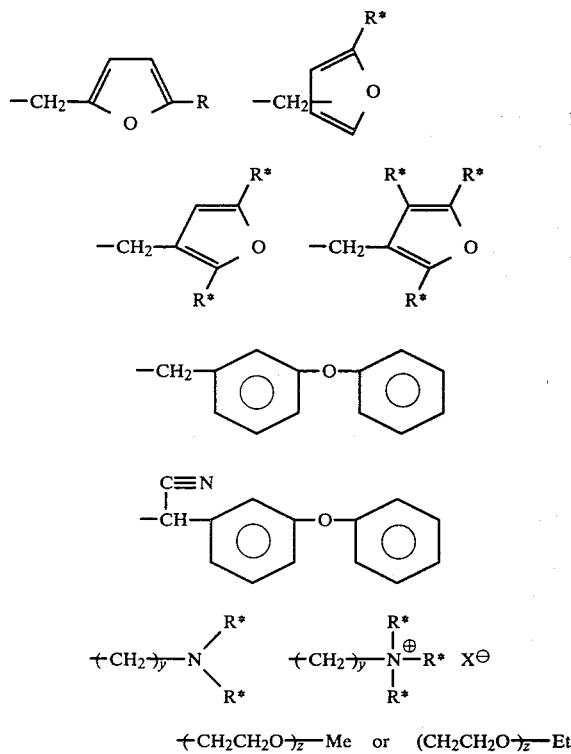

where $R^*$ is a $C_{1-4}$ alkyl, $C_{1-4}$ alkenyl, $C_{1-4}$ hydroxyalkyl, phenyl or benzyl, Me is methyl, Et is ethyl, y is an integer from 2 to 6, z is an integer from 1 to 10 and X represents an anion such as halide, hydroxide, sulfate, nitrate, acetate, alkylsulfate, alkylphosphate, fluoroborate and the like.

To obtain the products of this invention, 2-vinylcyclopropane-1,1-dicarboxylic acid or 2-ethylcyclopropane-1,1-dicarboxylic acid, the acid halide or lower alkyl ester thereof, are typically utilized. Whereas any process which is non-destructive to the cyclopropane ring and which does not result in decarboxylation of the gem carboxyl groups can be employed, the carboxylates of this invention are preferably obtained by transalcoholysis of a lower alkyl ester, preferably methyl or ethyl, of the cyclopropane dicarboxylic acid with an alcohol or mixture of alcohols.

Transalcoholysis of the resulting cyclopropane lower alkyl ester is carried out in accordance with conventional procedures. Lower alkyl 2-vinylcyclopropane-1,1-dicarboxylates and lower alkyl 2-ethylcyclopropane-1,1-dicarboxylates which can be used for the transalcoholysis reaction to obtain the novel products of the invention are readily obtained via classical or non-classical malonic ester condensation procedures. An especially useful process, in that it provides a convenient and commercially viable procedure for the preparation of lower alkyl esters of 2-vinylcyclopropane dicarboxylic acids, is the phase transfer process described in U.S. Pat. No. 4,252,739. This process involves reacting an alkylating agent with an activated methylene compound in the presence of an alkali metal compound, water and an onium compound, preferably a quaternary ammonium compound.

In addition to transalcoholysis, a cyclopropane carboxylic acid, mono- or di-, can also be directly reacted with an alcohol or alcohol mixture employing conventional esterification procedures and suitable conditions. Mono or dialkali salts of the aformentioned acids may also be reacted with suitable active halide compounds to produce the desired cyclopropyl esters. Mono- or di-acid halides of the vinyl- or ethylcyclopropane can also be reacted with the alcohol or corresponding alkali metal alkoxide.

Illustrative alcohols, or halides or alkoxides derived from these alcohols, which can be used to obtain the products of this invention in accordance with the above-mentioned procedures include but are not limited to the following:
2-methyl-1-pentanol
2-ethylhexanol
2-octanol
2,6-dimethyl-4-heptanol
dodecanol
hexadecanol
octadecanol
allyl alcohol
3-methyl-1-buten-3-ol
3-ethyl-1-buten-3-ol
3-methyl-3-penten-1-ol
1,4-pentadien-3-ol
5-cyclohexylidene-2-pentanol
2-methyl-2-hepten-6-ol
5,6-dimethyl-5-hepten-2-ol
6,10-dimethylundeca-5,9-dien-2-ol
3,7,11-trimethyldodeca-1,6,10-trien-3-ol
cyclopentanol
cyclohexanol
4-methylcyclohexanol
3-cyclobutyl-2-propen-1-ol
3-cyclopentyl-2-propen-1-ol
3-cyclohexyl-2-propen-1-ol
3-cycloheptyl-2-propen-1-ol
3-(4-chlorophenyl)-3-methyl-2-propen-1-ol
3-(4-methylphenyl)-3-methyl-2-propen-1-ol
3-(4-methylphenyl)-2-butyl-2-propen-1-ol
3-(4-methoxyphenyl)-1-methyl-2-propen-1-ol
3-(1-naphthyl)-2-propen-1-ol
3-(4-chloronaphth-1-yl)-2-propen-1-ol
3-(4-methylnaphth-1-yl)-2-propen-1-ol
benzyl alcohol
(3-phenoxyphenyl)carbinol
(3-thiophenyl)carbinol
2,4-dimethylbenzyl alcohol
2,4,6-trimethylbenzyl alcohol
4-allylbenzyl alcohol
2,6-dimethyl-4-allylbenzyl alcohol
4-(3'-methylbenzyl)benzyl alcohol
4-(2',4'-dimethylbenzyl)benzyl alcohol
2,6-dichlorobenzyl alcohol
benzhydrol
cinnamyl alcohol
p-methoxycinnamyl alcohol
2,4,5-trimethoxycinnamyl alcohol
p-benzylcinnamyl alcohol
p-benzyloxycinnamyl alcohol
m-bromocinnamyl alcohol
3-chloro-4-methoxycinnamyl alcohol
o-methoxycinnamyl alcohol
p-isopropoxycinnamyl alcohol p-phenoxycinnamyl alcohol
p-methylcinnamyl alcohol
p-(methylphenethyl)cinnamyl alcohol
phenol
cresol
eugenol
isoeugenol
thymol
α-hydroxyacetophenone
cyclohexylphenol
t-butylphenol
nonylphenol
naphthol
2-phenoxyethanol
diethylene glycol monomethyl ether
triethylene glycol monoethyl ether
monoethanol amine
diethanol amine
triethanol amine
N-aminoethylethanol amine
2-(2-aminoethoxy)ethanol
3-Bis(2-hydroxyethyl)aminopropylamine
N-hydroxyethylethylene diamine
N-methyldiethanol amine
2-(2-(3-aminopropoxy)ethoxy)ethanol
2-methylaminoethanol
2-dimethylaminoethanol
2-diethylaminoethanol
N-2-hydroxyethylacetamide
2-anilinoethanol
2-N-ethylanilinoethanol
1-dimethylamino-2-propanol
1-(2-aminoethylamino)-2-propanol
4-(2'-thenyl)benzyl alcohol
furfuryl alcohol
(3-furyl)carbinol
thiofurfuryl alcohol
4-(2'-furfuryl)benzyl alcohol
(5-benzyl-3-furyl)carbinol
2-(2',4'-dimethylbenzyl)-4-furfuryl alcohol
(5-benzyl-2-furyl)carbinol
(4-benzyl-5-methyl-2-furyl)carbinol
2-(4'-methylbenzyl)-5-furfuryl alcohol
(3-methyl-2-furyl)carbinol
(2-methyl-3-furyl)carbinol
(5-methyl-3-furyl)carbinol
(5-methyl-2-furyl)carbinol
(2,5-dimethyl-3-furyl)carbinol
(2,4,5-trimethyl-3-furyl)carbinol
(5-allyl-2-furyl)carbinol
(5-allyl-3-furyl)carbinol
5-hydroxymethyl-2,2'-difurylmethane
4-hydroxymethyl-2,2'-difurylmethane
(4,5-benzo-2-furyl)carbinol
(4,5-benzo-3-furyl)carbinol
5-phenoxy-2-thienyl alcohol
N-hydroxymethyl-3,4,5,6-tetrahydrophthalimide
N-hydroxymethyl phthalimide
N-hydroxymethyl thiophthalimide
N-hydroxymethyl-3,6-dihydrophthalimide
N-hydroxymethyl dimethylmaleimide
N-hydroxymethyl methylethylmaleimide
N-hydroxymethyl phenylmethylmaleimide
3-hydroxymethyl-5-benzyl-1,2,4-oxadiazole
1-benz-4-hydroxymethylpyrazole
3-methyl-2-cyclopenten-4-ol-1-one
2-allyl-3-methyl-2-cyclopenten-4-ol-1-one Compounds of this invention may also be made directly utilizing procedures known for reacting diester reagents with either an olefinic compound or active halide compound to form cyclopropane derivatives, such as classical or phase-transfer alkylation reactions, diazo insertion reactions, carbene insertion reactions, Wurtz reactions and Simmons-Smith reactions.

It will be evident to those skilled in the art that various geometric and stereo isomers of these compounds, and mixtures and racemates thereof, will exist. For example, by varying the process and reaction conditions by which the compound is prepared it is possible to impart preferential optical activity. Whereas the formula depicted above does not take into account isomeric forms, i.e. cis- and trans-configurations and dextro and levo forms, it is intended that the invention be construed to encompass all such forms and mixtures thereof.

The novel compounds of this invention are useful for a wide variety of applications, however, they are particularly useful as herbicides and insecticides. As employed herein, the term herbicide is used in its broadest sense to encompass any type of modification of plant growth including retardation of growth, defoliation, dessication, regulation, stimulation, dwarfing and, in some cases, killing the plant. In addition to treatment of established plants and emerging seedlings, the compounds of this invention can also be applied as a seed coating. The term insecticide is also used in the broad sense wherein it encompasses not only usage for the control of beetles, flies and mosquitos but also use for the control of spiders, lice, mites, ticks, nemotodes and other pests not classified as insects in the strict biological sense. Various isomeric forms will exhibit more activity than other isomers for certain of these applications.

The 2-vinyl- and 2-ethylcyclopropanedicarboxylates of this invention may be utilized as such, they may be chemically modified by further reaction, or they may be utilized in combination with other known active compounds to enhance the overall insecticidal/herbicidal effectiveness. The ability to develop synergistic insecticidal and herbicidal formulations is generally well recognized in this art and the use of combinations including the products of this invention may provide a means of enhancing the overall activity and/or selectivity of the resulting formulation and/or making the compositions more cost effective. The cyclopropane dicarboxylates may be formulated with an inert carrier or diluent or they may be prepared and utilized in the form of dusts, wettable powders, emulsions and the like.

The following examples illustrate more fully the preparation of the novel compounds of this invention and intermediates thereof and demonstrate the effectiveness of these products for herbicidal and insecticidal applications. These examples are illustrative only and are not intended as any limitation on the scope of the invention since numerous variations and modifications are possible and will be evident to those skilled in the art to which the invention pertains. All parts and percentages provided in the examples are on a weight percent basis unless otherwise indicated.

EXAMPLE I

Preparation of dimethyl 2-vinylcyclopropane-1,1-dicarboxylate: To a solution of 36.6 g (1.6 g-atom) of sodium in 500 ml of anhydrous ethanol was added 105.5 g (0.80 mol) of dimethyl malonate. After several minutes, while maintaining the temperature at 60° C., 250 ml anhydrous methanol was added to solubilize the precipated sodium malonate salt. The freshly prepared disodiomalonate methanol solution was added to 100.0 g (0.80 mol) trans 1,4-dichlorobutene-2 heated to 60°–70° C. at a rate to allow a gentle reflux in the condenser. When the addition was completed, the reaction mixture was refluxed with stirring for an additional 4 hours. The reaction mixture was then cooled to ambient temperature, filtered and the resulting filtrate concentrated. Distillation of the crude product under reduced pressure afforded 82 g (44.5%) of the desired product dimethyl 2-vinylcyclopropane-1,1-dicarboxylate. B.p. 73°–78° at 1.25 mm Hg; $n_D^{24}$ 1.4612; [lit. B.p. 71°–73° (1 mm); $n_D^{25}$ 1.4602].

Preparation of methyl (5-benzyl-3-furyl)methyl 2-vinylcyclopropane-1,1-dicarboxylate: Twenty grams (0.106 mol) (5-benzyl-3-furyl)carbinol was charged to a stirred glass reactor with 39 g (0.212 mol) dimethyl 2-vinylcyclopropane-1,1-dicarboxylate, 0.5 g hydroquinone, 0.5 g calcium acetate and 0.38 g dibutyltin diacetate and heated. After the temperature reached about 165° C., methanol began to distill from the reaction mixture and was collected by means of a suitable condenser-trap arrangement. When the transalcoholysis was essentially complete (3.2 g methanol collected; reaction temperature 182° C.) heating was terminated. Excess dimethyl 2-vinylcyclopropane-1,1-dicarboxylate was removed by distillation and the resulting crude light brown oil worked up to recover 12.6 g (35% yield) methyl (5-benzyl-3-furyl)methyl 2-vinylcyclopropane-1,1-dicarboxylate. B.p. 160°–162° C. at 0.018 mm Hg; $n_D^{21}$ 1.5335. Infrared and nuclear magnetic resonance spectra were consistent with the desired structure.

To demonstrate the utility of the methyl (5-benzyl-3-furyl)methyl 2-vinylcyclopropane-1,1-dicarboxylate prepared by the above reaction the product was topically applied to 6–7 day-old house flies, *Musca domestica*, and the mortality determined. One replicate of 10 flies was employed for the test. For the test the product was diluted to 0.5% in acetone and 1 microliter per gram of fly weight applied to the dorsum of each fly. Flies were inactivated by CO$_2$ for efficiency in handling. After 24 hours 50% mortality was achieved and there was 88% mortality after 48 hours. Similar insecticidal activity is observed when methyl (3-phenoxyphenyl)methyl 2-vinylcyclopropane-1,1-dicarboxylate obtained by the transalcoholysis of dimethyl 2-vinylcyclopropane-1,1-dicarboxylate with (3-phenoxyphenyl)carbinol is employed.

EXAMPLE II

Dimethyl 2-vinylcyclopropane-1,1-dicarboxylate (79.5 g; 0.432 mol) was combined with 21.2 g (0.216 mol) (3-furyl)carbinol and heated to 165°–183° C. in the presence of 1.0 g hydroquinone, 1.0 g calcium acetate and 0.75 g dibutyltin diacetate. When the transalcoholysis was essentially complete, as determined by the amount of methanol recovered, heating was terminated. Gas chromatographic analysis of the reaction mixture confirmed that essentially all of the (3-furyl)carbinol was consumed. The reaction mixture was diluted with an equal volume of ethyl ether, filtered to remove insoluble catalyst residue and vacuum distilled to recover 31 g (57.4% yield) crude methyl (3-furyl)methyl 2-vinylcyclopropane-1,1-dicarboxylate. B.p. 97°–105° C. at 0.018 mm Hg. Infrared and nuclear magnetic resonance spectra were consistent with the desired structure.

EXAMPLE III

A transalcoholysis reaction was carried out in a manner similar to that described for Example II using dimethyl 2-vinylcyclopropane-1,1-dicarboxylate (92 g; 0.5 mol) and furfuryl alcohol (24.5 g; 0.25 mol). When essentially all of the furfuryl alcohol was consumed, the reaction mixture was dissolved in ethyl ether and washed with aqueous potassium hydroxide (5%). The ether portion was dried over MgSO$_4$, filtered and vacuum distilled to obtain 21.63 g crude methyl (2-furyl)methyl 2-vinylcyclopropane-1,1-dicarboxylate. B.p. 91°–97° C. at 0.015 mm Hg. The distilled product (M.p. 58°–64° C.) was first recrystallized from methanol and then from a mixture of petroleum ether and methanol to obtain high purity methyl (2-furyl)methyl 2-vinylcyclopropane-1,1-dicarboxylate (translucent crystals melting at 67.5°–68.5° C.). The infrared spectra and nuclear magnetic resonance spectra were consistent with the desired product. Similar results are obtained when (5-methyl-2-furyl)carbinol, (5-allyl-3-furyl)carbinol and 5-hydroxymethyl-2,2'-difuryl methane are substituted for the furfuryl alcohol in the above reaction and all of these products are useful in insecticidal formulations.

EXAMPLE IV

Preparation of diethyl 2-vinylcyclopropane-1,1-dicarboxylate via the phase transfer process of U.S. Pat. No. 4,252,739: Fifty percent aqueous potassium hydroxide solution (168 g) was added dropwise to a vigorously stirred solution of 125 g (1.0 mol) trans 1,4-dichlorobutene-2, 80 g (0.50 mol) diethyl malonate and 3.2 g tricaprylylmethylammonium chloride while the temperature was maintained at 25°–30° C. When the addition was complete, the reaction mixture was stirred at ambient temperature for an additional five hours. Water was then added to the reaction mixture to completely dissolve the suspended salts in the aqueous phase. The phase layers were separated and the aqueous portion extracted three times with ethyl ether. Distillation of the combined organic solutions gave 21.3 g of the desired diethyl 2-vinylcyclopropane-1,1-dicarboxylate. B.p. 64°–66° C. (0.15 mm); $n_D^{27°}$ 1.4512; [lit. b.p. 69°–72° C. (0.5 mm); $n_D^{19°}$ 1.4528].

Diethyl 2-vinylcyclopropane-1,1-dicarboxylate (33.77 g; 0.159 mol) prepared following the above procedure and 10 g (0.053 mol) (5-benzyl-3-furyl)carbinol were reacted using sodium ethoxide catalyst. The sodium ethoxide was prepared by the addition of 5 ml anhydrous ethanol to 8 ml dry toluene containing 0.2 g sodium metal in small pieces. The diethyl 2-vinylcyclopropane-1,1-dicarboxylate and (5-benzyl-3-furyl)carbinol were combined and added to the sodium ethoxide/toluene mixture and the reaction mixture heated to reflux. After the theoretical amount of ethanol was collected, the reaction mixture was cooled, added to 100 ml hexane and washed with water until neutral. After drying over MgSO$_4$, the hexane was removed under vacuum and the resulting product (32.6 g) vacuum distilled to remove unreacted diethyl 2-vinylcyclopropane-1,1-dicarboxylate. The pot residue (13.46 g) was passed through a column (1 inch; 70 g neutral alumina; 75 pentane:25 ether) to obtain 7.76 g ethyl (5-benzyl-3-furyl)methyl 2-vinylcyclopropane-1,1-dicarboxylate (97% pure).

The ethyl (5-benzyl-3-furyl)methyl 2-vinylcyclopropane-1,1-dicarboxylate was evaluated to determine its toxicity against mosquito larvae, *Aedes aegypti*. A 10% stock solution in acetone was prepared and diluted with deionized water to a concentration of 1000 ppm. An equal amount of piperonyl butoxide, a widely used adjuvant for insecticidal compounds, was included with the ethyl (5-benzyl-3-furyl)methyl 2-vinylcyclopropane-1,1-dicarboxylate. The mosquito larvae were exposed in 40 mls of solution and after 6 hours 60% mortality was observed. Total kill (100% mortality) was noted after 24 hours.

EXAMPLE V

Following the procedure of Example IV ethyl (5-benzyl-2-furyl)methyl 2-vinylcyclopropane-1,1-dicarboxylate was prepared by the transalcoholysis of 28.75 g (0.135 mol) diethyl 2-vinylcyclopropane-1,1-dicarboxylate with 8.5 g (0.045 mol) (5-benzyl-2-furyl)carbinol. The reaction was carried out in toluene using sodium methoxide as the catalyst. At the completion of the reaction and after removal of excess diethyl 2-vinylcyclopropane-1,1-dicarboxylate, 16.5 g crude product was recovered. Work up of the crude product using the chromatographic procedure of Example IV yielded 7.7 g (48.6% yield) ethyl (5-benzyl-2-furyl)methyl 2-vinylcyclopropane-1,1-dicarboxylate (97.7% pure). Similar results are obtained when (4,5-benzo-3-furyl)carbinol is substituted for the (5-benzyl-2-furyl)carbinol in the above reaction.

EXAMPLE VI

Employing a procedure similar to that of Example IV diethyl 2-vinylcyclopropane-1,1-dicarboxylate was reacted with a polyalkoxylated alcohol in the presence of sodium ethoxide catalyst. For the process 33.77 g (0.159 mol) diethyl 2-vinylcyclopropane-1,1-dicarboxylate and 7.12 g (0.053 mol) 2-(2-ethoxyethoxy)ethanol were heated at reflux until the theoretical amount of ethanol was recovered. After removal of unreacted diethyl 2-vinylcyclopropane-1,1-dicarboxylate (19.63 g), 8.4 g crude ethyl 2-(2-ethoxyethoxy)ethyl 2-vinylcyclopropane-1,1-dicarboxylate was obtained. Redistillation of the crude product provided 4.9 g high purity 2-(2-ethoxyethoxy)ethyl 2-vinylcyclopropane-1,1-dicarboxylate. B.p. 110°–112° C. at 0.01 mm Hg; $n_D^{24.5}$ 1.4608. Infrared and nuclear magnetic resonance spectra were consistent with the desired structure.

EXAMPLE VII

Employing a phase transfer process similar to that described in Example I, diisopropyl 2-vinylcyclopropane-1,1-dicarboxylate was prepared by reacting 125 g (1.0 mol) trans 1,4-dichlorobutene-2, 94 g (0.50 mol) diisopropyl malonate and 158 g 50% aqueous potassium hydroxide. Tricaprylyl methylammonium chloride (3.2 g) was employed as the catalyst. During the reaction and as necessary, cooling was provided to maintain the temperature of the reaction mixture at 25°–30° C. After 5 hours the reaction was terminated and, upon workup, 184 g (67.2% yield) diisopropyl 2-vinylcyclopropane-1,1-dicarboxylate (B.p. 77°–78° C. at 0.5 mm Hg; $n_D^{24}$ 1.4482) obtained. Twenty-four grams (0.1 mol) of the diisopropyl 2-vinylcyclopropane-1,1-dicarboxylate were combined with 9.4 g (0.05 mol) (5-benzyl-3-furyl)carbinol and the resulting solution slowly added to a reactor containing sodium ethoxide or toluene. The sodium ethoxide was obtained by reacting 0.2 g sodium with 5 ml absolute ethanol in 100 ml toluene. The addition, subsequent reaction and recovery of the resulting product followed the procedure of Example IV. Isopropyl (5-benzyl-3-furyl)methyl 2-vinylcyclopropane-1,1-dicarboxylate (B.p. 170°–183° C. at 0.02 mm Hg; $n_D^{28}$ 1.5219) was obtained in 36.9% yield. Infrared and nuclear magnetic resonance spectra were consistent with the desired structure.

EXAMPLE VIII

Di-n-butyl 2-vinylcyclopropane-1,1-dicarboxylate (B.p. 101°–104° C. (0.30 mm Hg); $n_D^{24}$ 1.4556) was prepared in accordance with the procedure of Example I and 26.8 g (0.1 mol) of the product reacted with 9.40 g (0.05 mol) (5-benzyl-3-furyl)carbinol following the procedure of Example IV. n-Butyl (5-benzyl-3-furyl)methyl 2-vinylcyclopropane-1,1-dicarboxylate (B.p. 219°–228° C. at 0.01–0.008 mm Hg; $n_D^{27}$ 1.5207) was obtained in good yield (30.5%) upon workup and vacuum distillation of the reaction product.

EXAMPLE IX

To a suspension of sodium ethoxide in toluene were added 339.2 g (1.6 mol) diethyl 2-vinylcyclopropane-1,1-dicarboxylate and 285.3 g (3.2 mol) N,N-dimethylaminoethanol. The reaction mixture was heated at reflux for six hours while removing toluene/ethanol azeotrope. The reaction mixture was then cooled, filtered and the resulting filtrate concentrated on a rotary evaporator. Distillation of the crude product through a spinning band apparatus under reduced pressure afforded 162.4 g (46.8%) of a monoamine product, ethyl 2-(N,N-dimethylamino)ethyl 2-vinylcyclopropane-1,1-dicarboxylate [B.p. 99°–102° C. (0.07–0.10 mm Hg)], and 115.1 g (28.4%) of the diamine, di-2-(N,N-dimethylamino)ethyl 2-vinylcyclopropane-1,1-dicarboxylate [B.p. 127°–131° C. (0.11–0.20 mm Hg)]. Similar results are obtained when the reaction is repeated except that N-methyl diethanol amine and 2-(2-(3-aminopropoxy)ethoxy) ethanol are substituted for the N,N-dimethylaminoethanol.

EXAMPLE X

Quaternary salts of ethyl 2-(N,N-dimethylamino)ethyl 2-vinylcyclopropane-1,1-dicarbxoylate prepared in Example IX were obtained by reacting the product with a molar excess of various alkyl halides in ethanol. The reaction mixture was stirred at ambient temperature overnight, excess ethanol removed and the resulting solid or oil then washed with anhydrous ethyl ether to remove any remaining starting agents. The resulting salts were then dried under reduced pressure at room temperature. In this manner, ethyl 2-(N,N-dimethylamino)ethyl 2-vinylcyclopropane-1,1-dicarboxylate was quaternized using methyl chloride, methyl iodide and benzyl chloride with the following results: ethyl 2-(N,N,N-trimethylamino)ethyl 2-vinylcyclopropane-1,1-dicarboxylate chloride (identified as compound XA) was obtained in 95% yield as a light yellow, glassy solid; ethyl 2-(N,N,N-trimethylamino)ethyl 2-vinylcyclopropane-1,1-dicarboxylate iodide (compound XB) was obtained in 81% yield as a light yellow deliquescent solid; and ethyl 2-(N,N-dimethyl-N-benzylamino)ethyl 2-vinylcyclopropane-1,1-dicarboxylate chloride (compound XC) was obtained in 74.1% yield as a light tan solid.

Quaternized compounds XA, XB and XC were demonstrated to be effective plant growth regulators. Plant growth studies were conducted on Tenderbest bush beans which were grown in 4⅛" O.D.×4" clay pots. The plants were grown at 26°–27° C. in commercial potting soil under "Duro-Lite Vita Lite" fluorescent light tubes. The lamps were on a 12-hour lighting cycle and were maintained 12" from the tops of the plants (adjusted for height every other day).

For the test, 10–11 day old plants having two fully developed extended smooth leaves (3.5–5.0 cm across) and with trifoliate leaves still folded in a terminal bud, were uniformly sprayed with an aqueous solution containing the product being tested and 1% by weight of a wetting agent (polyoxyethylene sorbitan monolaurate). The concentration of the compound being tested in the solution was determined as a function of solution necessary to spray a 2 sq. ft. area in a 30 second period with a known weight amount of the test compound expressed in pounds per acre. After spraying, the growth of the plants (uniformly watered so that the surface soil was never allowed to go dry) was recorded after four days. The length of the second internode was measured and compared with the second internode growth of unsprayed control plants. Percent dwarfing was then determined in accordance with the formula $$100 - \left[ \frac{\text{growth 2nd internode (mm)} - \text{treated plants}}{\text{growth 2nd internode (mm)} - \text{untreated plants}} \times 100 \right] = \% \text{ dwarfing}$$

Results were as follows:

|  | PERCENT DWARFING | | |
| --- | --- | --- | --- |
|  | 2½ lb/acre | 5 lb/acre | 10 lb/acre |
| Compound XA | 76 | 80 | 84 |
| Compound XB | 54 | 67 | 79 |
| Compound XC | 49 | 57 | 58 |

EXAMPLE XI

2-Vinylcyclopropane-1-carbomethoxy-1-carboxylic acid chloride (B.p. 39° C. at 0.2 mm Hg; $n_D^{21}$ 1.4765) was prepared from the corresponding dimethyl ester and, following the procedure of British Pat. No. 1,338,432, converted to methyl 2-(N,N,N-trimethylamino)ethyl 2-vinylcyclopropane-1,1-dicarboxylate chloride.

EXAMPLE XII

Following the procedure described in Example X the diamine product of Example IX was reacted with a molar excess of methyl chloride, methyl iodide and benzyl chloride to form the respective quaternary salts di-2-(N,N,N-trimethylamino)ethyl 2-vinylcyclopropane-1,1-dicarboxylate dichloride (light yellow glass), di-2-(N,N,N-trimethylamino)ethyl 2-vinylcyclopropane-1,1-dicarboxylate diiodide (99.6% yield; while crystals), and di-2-(N,N-dimethyl-N-benzylamino)ethyl 2-vinylcyclopropane-1,1-dicarboxylate dichloride (91.7% yield; white deliquescent crystals).

EXAMPLE XIII

Acid salt aqueous solutions of the monoamine product of Example IX were prepared by dispersing the ethyl 2-(N,N-dimethylamino)ethyl 2-vinylcyclopropane-1,1-dicarboxylate in water and then acidifying with a sufficient quantity of the appropriate acid. In this manner the hydrochloride, acetate and phosphate salts of ethyl 2-(N,N-dimethylamino)ethyl 2-vinylcyclopropane-1,1-dicarboxylate were prepared.

EXAMPLE XIV

Diethyl 2-vinylcyclopropane-1,1-dicarboxylate (5 g; 0.024 mol) was combined with 8.8 g (0.047 mol) tosyl hydrazine in 20 mls diglyme and the mixture heated with agitation to reflux for one hour. The reaction mixture was then allowed to cool and 2.73 g crude product obtained after washing with water and petroleum ether. The purified diethyl 2-ethylcyclopropane-1,1-dicarboxylate, obtained by distillation, contained 61.89% carbon and 8.33% hydrogen (calculated 61.66% C, 8.47% H) and the nuclear magnetic resonance spectra verified that the product was completely reduced.

EXAMPLE XV

Diethyl 2-ethylcyclopropane-1,1-dicarboxylate (21.48 g; 0.1 mol) prepared in accordance with the procedure of Example XIV was reacted with 45 g (0.5 mol) N,N-dimethylaminoethanol in the presence of a small amount of dibutyltin oxide catalyst. The reaction mixture was heated at 135° C. and ethanol removed during the course of the reaction by means of a Dean-Stark trap. A mixture of monoamine and diamine products was obtained, which upon fractional distillation using a spinning band apparatus, afforded 8.4 g ethyl 2-(N,N-dimethylamino)ethyl 2-ethylcyclopropane-1,1-dicarboxylate [B.p. 102°–105° C. (0.07–0.10 mm Hg)] and 4.75 g di-2-(N,N-dimethylamino)ethyl 2-ethylcyclopropane-1,1-dicarboxylate. [B.p. 130°–134° C. (0.11–0.20 mm Hg)]. In accordance with the procedure of Example X the monoamine and diamine products were quaternized with methyl chloride, methyl iodide, benzyl chloride and diethylsulfate and the resulting quaternary salts proved to be effective herbicides.

I claim:

1. A compound of the formula

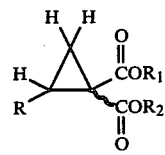

wherein R is an ethyl or vinyl group, $R_1$ and $R_2$ are hydrocarbon radicals containing from 1 to 30 carbon atoms and selected from the group consisting of aliphatic, cycloaliphatic and aromatic radicals, with the proviso that $R_1$ and $R_2$ cannot both be aliphatic hydrocarbon radicals.

2. A compound according to claim 1 wherein the hydrocarbon radical is an aliphatic radical containing from 1 to 20 carbon atoms, the cycloaliphatic radical contains from 5 to 20 carbon atoms and corresponds to the formula

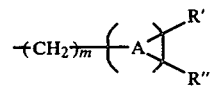

where m is an integer from 0 to 8, A represents a nonaromatic 5- or 6-membered carbon ring system and R' and R" are hydrogen, $C_{1-8}$ alkyl, $C_{1-8}$ alkenyl, phenyl or benzyl, and the aromatic radical contains from 6 to 20 carbon atoms and corresponds to the formula

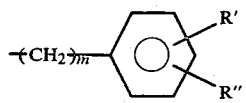

wherein m, R' and R" are the same as defined above.

3. A compound according to claim 2 wherein the aliphatic radical contains no more than one double bond for every 4 carbon atoms, the cycloaliphatic radical is an unsubstituted or mono- $C_{1-8}$ alkyl- or alkenyl-substituted cyclopentyl, cyclopentenyl, cyclohexyl, cyclohexenyl, or cyclohexa-2,4-dienyl group and the aromatic radical is phenyl, $C_{1-8}$ alkyl- or alkenyl-substituted phenyl, benzyl or $C_{1-8}$ alkyl- or alkenyl-substituted benzyl.

4. A compound of the formula

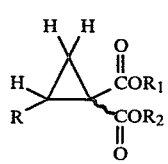

wherein $R_1$ and $R_2$ are heteroalkyl or heterocyclic radicals containing from 3 to 20 carbon atoms selected from the group

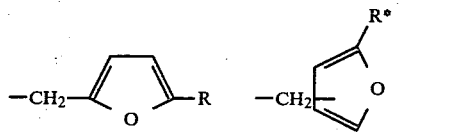

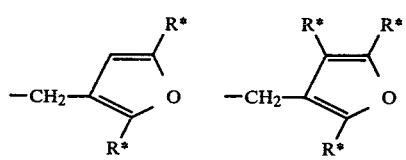

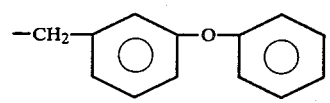

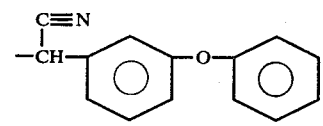

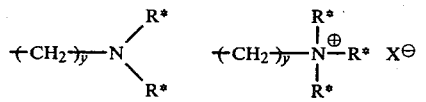

wherein R* is a $C_{1-4}$ alkyl, $C_{1-4}$ alkenyl, $C_{1-4}$ hydroxyalkyl, phenyl or benzyl, Me is methyl, Et is ethyl, y is an integer from 2 to 6, z is an integer from 1 to 10 and X is halide, hydroxide, sulfate, nitrate, acetate, alkylsulfate, alkylphosphate or fluoroborate.

5. A compound of the formula

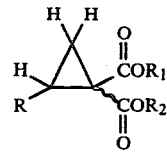

wherein $R_1$ is a hydrocarbon radical containing from 1 to 30 carbon atoms and selected from the group consisting of aliphatic, cycloaliphatic and aromatic radicals and $R_2$ is a heteroalkyl or heterocyclic radical containing from 3 to 20 carbon atoms and selected from the group

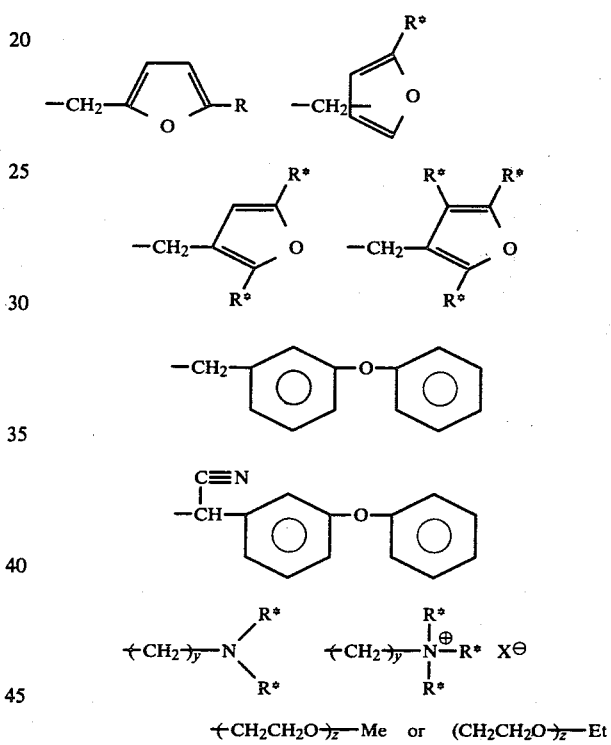

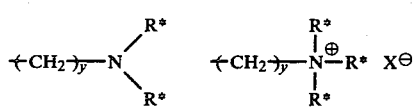

wherein R* is a $C_{1-4}$ alkyl, $C_{1-4}$ alkenyl, $C_{1-4}$ hydroxyalkyl, phenyl or benzyl, Me is methyl, Et is ethyl, y is an integer from 2 to 6, z is an integer from 1 to 10 and X is halide, hydroxide, sulfate, nitrate, acetate, alkylsulfate, alkylphosphate or fluoroborate.

6. A compound according to claim 5 wherein $R_1$ is an aliphatic radical containing no more than one double bond for every 4 carbon atoms, an unsubstituted or mono- $C_{1-8}$ alkyl- or alkenyl- substituted cyclopentyl, cyclopentenyl, cyclohexyl, cyclohexenyl, or cyclohexa-2,4-dienyl group, phenyl, $C_{1-8}$ alkyl- or alkenyl- substituted phenyl, benzyl or $C_{1-8}$ alkyl- or alkenyl- substituted benzyl.

7. A compound according to claim 6 wherein $R_1$ is an alkyl group having 1 to 4 carbon atoms.

* * * * *

UNITED STATES PATENT AND TRADEMARK OFFICE
CERTIFICATE OF CORRECTION

PATENT NO. : 4,380,656            Page 1 of 2
DATED     : April 19, 1983
INVENTOR(S) : Richard G. Fayter, Jr.

It is certified that error appears in the above-identified patent and that said Letters Patent are hereby corrected as shown below:

Column 1, line 16, insert "the" after --- of ---; line 34, "dicarboxylate" should read ---decarboxylate---.

Column 2, line 10, 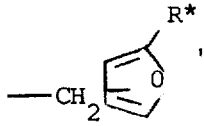 should read 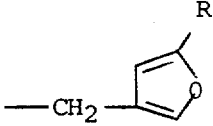 ;

line 36, "(CH$_2$CH$_2$O)$_z$—Et" should read --- —(CH$_2$CH$_2$O)$_z$—Et ---.

Column 4, line 25, "esters" should read --- ethers ---.

Column 5, line 10, 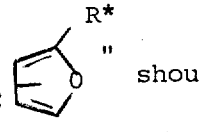 should read 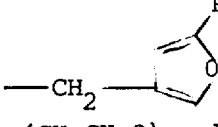 ---;

line 34, "(CH$_2$CH$_2$O)$_z$—Et" should read --- —(CH$_2$CH$_2$O)$_z$—Et ---.

Column 11, line 53, "Tricaprylyl methylammonium" should read
--- Tricaprylylmethylammonium ---; line 64, "or" should read
--- in ---.

Column 12, line 42, "dicarbxoylate" should read --- dicarboxylate ---.

Column 13, line 57, "while" should read --- white ---.

UNITED STATES PATENT AND TRADEMARK OFFICE
CERTIFICATE OF CORRECTION

PATENT NO. : 4,380,656
DATED : April 19, 1983
INVENTOR(S) : Richard G. Fayter, Jr.

It is certified that error appears in the above-identified patent and that said Letters Patent are hereby corrected as shown below:

Column 15, line 35, "—CH$_2$—[furan ring with R*]" should read --- —CH$_2$—[furan ring with R*] ---;

line 59, "(CH$_2$CH$_2$O)$_z$—Et" should read --- —(CH$_2$CH$_2$O)$_z$—Et ---.

Column 16, line 21, "—CH$_2$—[furan ring with R*]" should read --- —CH$_2$—[furan ring with R*] ---;

line 46, "(CH$_2$CH$_2$O)$_z$—Et" should read --- —(CH$_2$CH$_2$O)$_z$—Et ---.

Signed and Sealed this

Sixth Day of September 1983

[SEAL]

Attest:

GERALD J. MOSSINGHOFF

Attesting Officer    Commissioner of Patents and Trademarks